(12) United States Patent
Thum et al.

(10) Patent No.: US 7,855,265 B2
(45) Date of Patent: Dec. 21, 2010

(54) USE OF ESTER-MODIFIED ORGANOPOLYSILOXANES FOR PRODUCING COSMETIC OR PHARMACEUTICAL COMPOSITIONS

(75) Inventors: Oliver Thum, Ratingen (DE); Michael Ferenz, Essen (DE); Christian Hartung, Essen (DE); Jurgen Meyer, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 332 days.

(21) Appl. No.: 12/198,574

(22) Filed: Aug. 26, 2008

(65) Prior Publication Data

US 2009/0062459 A1 Mar. 5, 2009

(30) Foreign Application Priority Data

Aug. 29, 2007 (DE) ........................ 10 2007 041 028

(51) Int. Cl.
*C08G 77/12* (2006.01)
(52) U.S. Cl. .......................................... 528/31; 528/26
(58) Field of Classification Search ................... 528/31, 528/26
See application file for complete search history.

(56) References Cited

U.S. PATENT DOCUMENTS

| 5,226,923 | A | 7/1993 | O'Lenick, Jr. |
| 5,306,838 | A | 4/1994 | Shioya et al. |
| 7,196,153 | B2 | 3/2007 | Burkhart et al. |
| 2006/0155089 | A1 | 7/2006 | Ferenz et al. |
| 2006/0155090 | A1 | 7/2006 | Ferenz |
| 2006/0165627 | A1 | 7/2006 | Allef et al. |
| 2006/0188455 | A1 | 8/2006 | Ferenz et al. |
| 2006/0188456 | A1 | 8/2006 | Ferenz et al. |
| 2006/0204468 | A1 | 9/2006 | Allef et al. |
| 2007/0059539 | A1 | 3/2007 | Doehler et al. |
| 2007/0092470 | A1 | 4/2007 | Allef et al. |
| 2007/0100153 | A1 | 5/2007 | Brueckner et al. |
| 2007/0128143 | A1 | 6/2007 | Gruning et al. |
| 2007/0178144 | A1 | 8/2007 | Hameyer et al. |
| 2007/0184006 | A1 | 8/2007 | Ferenz et al. |
| 2008/0004357 | A1 | 1/2008 | Meyer et al. |
| 2008/0027202 | A1 | 1/2008 | Ferenz et al. |
| 2008/0064782 | A1 | 3/2008 | Doehler et al. |
| 2008/0108709 | A1 | 5/2008 | Meyer et al. |

FOREIGN PATENT DOCUMENTS

| DE | 1165574 | | 8/1960 |
| DE | 3740186 | A1 | 1/1989 |
| DE | 3938140 | C2 | 8/1991 |
| DE | 4009347 | A1 | 9/1991 |
| DE | 4238081 | C2 | 7/1993 |
| DE | 4204321 | A1 | 8/1993 |
| DE | 4229707 | A1 | 3/1994 |
| DE | 4229737 | C2 | 3/1994 |
| DE | 4309372 | C2 | 9/1994 |
| DE | 4324219 | C2 | 1/1995 |
| DE | 19855934 | A1 | 6/2000 |
| DE | 102006005100 | A1 | 8/2007 |
| EP | 0666732 | B1 | 8/1995 |
| EP | 1887024 | A1 | 2/2008 |
| EP | 1 816 154 | A1 | 4/2009 |

OTHER PUBLICATIONS

"Rompp Lexikon Chemie, 10. Auflage" 1997, Georg Thieme Verlag, Stuttgart, New York, pp. 1149-1150, together with English-language translation of pp. 1149-1150.
Finkel, P. "Formulierung kosmetischer Sonnenschutzmittel," SÖFW-Journal, 1996, pp. 543-548, 122.
U.S. Appl. No. 12/168,350, entitled, "Enzyme Preparations for Use as Biocatalysts," filed on Jul. 7, 2008.
U.S. Appl. No. 12/179,944, entitled, "Linear Polydimethylsiloxane-Polyoxyalkylene Block Copolymers Linked via SiC Groups and via Carboxylic Ester Groups, a Process for Preparing Them and Their Use," filed on Jul. 25, 2008.
U.S. Appl. No. 12/210,348, entitled, "Novel Siloxane-Containing Block Copolymers, Process for Their Preparation and Their Use for Lubricants," filed on Sep. 15, 2008.
U.S. Appl. No. 12/132,307 entitled, "Stable, Low Viscosity Cosmetic Compositions," filed on Jun. 3, 2008, first named inventor: Klaus Jenni.

*Primary Examiner*—Kuo-Liang Peng
(74) *Attorney, Agent, or Firm*—Scully, Scott, Murphy & Presser, P.C.

(57) ABSTRACT

The invention relates to emulsifier systems containing ester-modified, polyether-free organopolysiloxanes, to their use, in particular the production of cosmetic, dermatological or pharmaceutical formulations and also of care and cleaning compositions, and also the products themselves produced with the help of the emulsifier systems.

17 Claims, No Drawings

USE OF ESTER-MODIFIED ORGANOPOLYSILOXANES FOR PRODUCING COSMETIC OR PHARMACEUTICAL COMPOSITIONS

FIELD OF THE INVENTION

The invention relates to emulsifier systems which include ester-modified organopolysiloxanes, and to cosmetic, dermatological or pharmaceutical formulations which contain these emulsifier systems. The present invention also relates to the use of ester-modified organopolysiloxanes for producing cosmetic or pharmaceutical emulsions or dispersions.

BACKGROUND OF THE INVENTION

Organomodified siloxanes are used in a very wide variety of applications. The properties of organomodified siloxanes can be adjusted in a targeted manner through the nature of the modification, and also through the modification denseness.

Thus, for example, using allyl polyethers, organophilic or non-ionic hydrophilic groups can be bonded to a siloxane backbone. Such compounds are used, for example, as polyurethane foam stabilizers, as antifoams in propellants or as additives in paints and coatings.

Through reaction with alpha ($\alpha$)-olefins the siloxane is linked to hydrophobic groups. The resulting silicone waxes serve, for example, as an additive in personal care applications.

In many fields of application, it is evident that the effect of the siloxane depends decisively on the compatibility with the corresponding formulation.

Suitable cosmetic emulsifiers are, for example, siloxanes which, besides aliphatic groups based on $\alpha$-olefins, contain polyethers. See, for example, the commercial product ABIL EM 90 from Goldschmidt GmbH, Germany.

Since polyether-containing compounds have recently been the subject of increased criticism, there is a need for siloxane-based emulsifiers which contain no polyether groups, but at the same time have good emulsifying properties.

As such there is a need for providing new types of polyether-free, organomodified siloxanes which can be used as high-performance emulsifiers.

SUMMARY OF THE INVENTION

The invention provides emulsifier systems which are polyether-free, and include ester-modified organopolysiloxanes, and to cosmetic, dermatological or pharmaceutical formulations which contain these emulsifier systems. The present invention also relates to the use of ester-modified organopolysiloxanes for producing cosmetic or pharmaceutical emulsions or dispersions.

Surprisingly, the applicant has found that ester-modified organopolysiloxanes of general formula (I) can be used as high-performance emulsifiers. Specifically, general formula (I) is as follows:

where
N is a+b+c+d+e+f+2=20 to 250, preferably 50 to 150,
a is 1 to 230, preferably 10 to 130,
b is 1 to 100, preferably 5 to 30,
c is 1 to 100, preferably 5 to 30,
d is 0 to 50, preferably 0,
e is 0 to 10, preferably 0,
f is 0 to 10, preferably 0,
$R^1$ independently of the others is identical or different and is selected from the following groups: saturated or unsaturated, optionally branched alkyl groups having 1 to 30 carbon atoms, alkaryl radicals having 7 to 30 carbon atoms, and aryl radicals having 6 to 30 carbon atoms, preferably alkyl groups having 1 to 4 carbon atoms or phenyl, in particular methyl,
$R^2$ independently of the others is identical or different and is selected from the following groups: $R^1$, $R^3$, $R^4$ or $R^5$, preferably $R^1$,
$R^3$ independently of the others is identical or different ester radicals of the general formula (Ia)

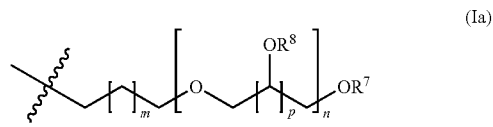

where
m is 1 to 4, preferably 1 or 4,
n is 0 or 1,
p is 0 or 1, preferably 0,
$R^7$ is the acyl radicals of monobasic, saturated or unsaturated, linear or branched fatty acids having 6 to 30 carbon atoms, in particular having 8 to 22 carbon atoms,
$R^8$ is hydrogen or $R^7$, preferably hydrogen,
$R^4$ is the radicals of the general formula (Ib)

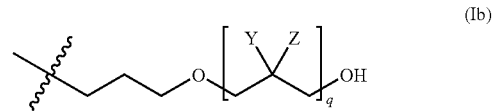

where
q is 1 to 20,
Y and Z independently of one another are identical or different radicals from the group —H, —OH, —$CH_3$, —$CH_2CH_3$ or —$CH_2OH$, where at least one radical must be from the group —OH or —$CH_2OH$,
$R^5$ independently of the others is saturated or unsaturated, optionally branched alkyl groups having 1 to 30 carbon atoms or alkaryl radicals having 7 to 30 carbon atoms, preferably alkyl groups having 6 to 22 carbon atoms,

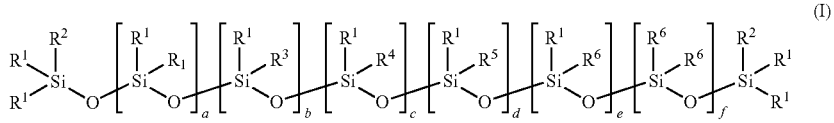

$R^6$ independently of the others is identical or different radicals of the general formula (Ic)

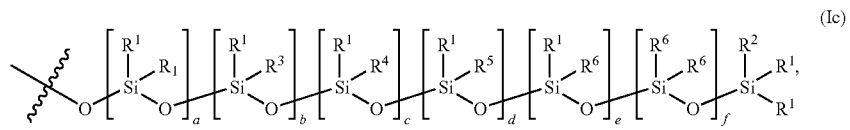
(Ic)

where a, b, c, d, e, f, $R^1$, $R^2$, $R^3$, $R^4$, $R^5$ and $R^6$ are as defined above.

The invention therefore provides emulsifier systems which comprise ester-modified organopolysiloxanes of the general formula (I).

DETAILED DESCRIPTION OF THE INVENTION

As stated above, the present invention provides emulsifier systems which are polyether-free, and include ester-modified organopolysiloxanes of general formula (I), and to cosmetic, dermatological or pharmaceutical formulations which contain these emulsifier systems. The present invention also relates to the use of ester-modified organopolysiloxanes for producing cosmetic or pharmaceutical emulsions or dispersions.

One advantage of the inventive emulsifier systems is that naturally occurring fatty acids and thus renewable raw materials can be used; these offer favorable access to renewable hydrophobic components which have hitherto not been used in siloxane-based emulsifiers. In addition, the broad palette of commercially available fatty acids offers the possibility, through careful selection of the acyl radicals, of further finely adjusting the properties of the inventive emulsifiers.

The emulsifier systems according to the invention are described below by way of example without any intention to restrict the invention to these exemplary embodiments. Where ranges, general formulae or compound classes are given below, then these are intended to include not only the corresponding ranges or groups of compounds that are explicitly mentioned, but also all part ranges and part groups of compounds which are obtained by removing individual values (ranges) or compounds. If documents are cited in the course of the present description, then their content, in its entirety, is to form part of the disclosure content of the present invention. If, in the course of the present invention, compounds such as, for example, organomodified polysiloxanes, are described which can have the various units in plurality, then these can occur in random distribution (random oligomer) or arranged (block oligomer) in these compounds. Data regarding the number of units in such compounds are to be understood as meaning the average, averaged over all of the corresponding compounds. Within the scope of this invention, emulsifier system is to be understood as meaning an emulsifier which consists at least of one substance of the general formula (I) and optionally at least one coemulsifier.

The invention provides emulsifier systems comprising siloxanes of the general formula (I) modified with organic esters where
N is a+b+c+d+e+f+2=20 to 250, preferably 50 to 150,
a is 1 to 230, preferably 10 to 130,
b is 1 to 100, preferably 5 to 30,
c is 1 to 100, preferably 5 to 30,
d is 0 to 50, preferably 0,
e is 0 to 10, preferably 0,
f is 0 to 10, preferably 0,
$R^1$ independently of the others is identical or different and is selected from the following group: saturated or unsaturated, optionally branched alkyl groups having 1 to 30 carbon atoms, alkaryl radicals having 7 to 30 carbon atoms, and aryl radicals having 6 to 30 carbon atoms, preferably alkyl groups having 1 to 4 carbon atoms or phenyl, in particular methyl,
$R^2$ independently of the others is identical or different and is selected from the following group: $R^1$, $R^3$, $R^4$ or $R^5$, preferably $R^1$,
$R^3$ independently of the others is identical or different ester radicals of the general formula (Ia)

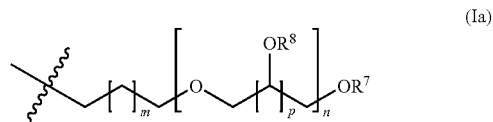
(Ia)

where
m is 1 to 4, preferably 1 or 4,
n is 0 or 1,
p is 0 or 1, preferably 0,
$R^7$ is the acyl radicals of monobasic, saturated or unsaturated, linear or branched fatty acids having 6 to 30 carbon atoms, in particular having 8 to 22 carbon atoms,
$R^8$ is hydrogen or $R^7$, preferably hydrogen,
$R^4$ is the radicals of the general formula (Ib)

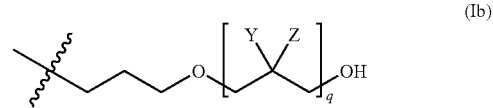
(Ib)

where
q is 1 to 20,
Y and Z independently of one another are identical or different radicals from the group —H, —OH, —CH$_3$, —CH$_2$CH$_3$ or —CH$_2$OH, where at least one radical must be from the group —OH or —CH$_2$OH,

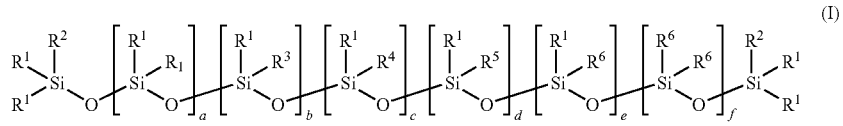
(I)

$R^5$ independently of the others is saturated or unsaturated, optionally branched alkyl groups having 1 to 30 carbon atoms or alkaryl radicals having 7 to 30 carbon atoms, preferably alkyl groups having 6 to 22 carbon atoms, $R^6$ independently of the others is identical or different radicals of the general formula (Ic)

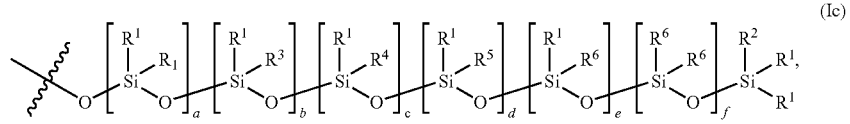

where a, b, c, d, e, f, $R^1$, $R^2$, $R^3$, $R^4$, $R^5$ and $R^6$ are as defined above.

In a preferred embodiment, m is 1 and n is 1. In a further preferred embodiment, m is 4 and n is 0.

Radicals according to the general formula (Ib) can, in particular, be compounds where q is 1,
Y is —OH and
Z is —H, or q is 1,
Y is —CH$_2$OH and
Z is —CH$_2$CH$_3$, or q is 2 to 20, preferably 3 to 10,
Y is —OH and
Z is —H.

In this regard, the person skilled in the art is aware that the latter case defines compounds derived from polyglycerol, which may also have linkages other than the 1,3 linkages indicated in formula (Ib). These may, for example, be technical-grade polyglycerol mixtures that can be obtained, for example, by alkaline-catalyzed condensation of glycerol at elevated temperatures, from which fractions with the desired degree of condensation can be obtained, if necessary by distillation methods.

Polyglycerols which can be obtained in another way, e.g., from epichlorohydrin, glycidol or glycerol, and are sold by Daicel or Solvay can also be used.

In the case of the acyl radical used as radical $R^7$, natural fatty acids based on natural vegetable or animal oils can be used. Preference is given to using natural fatty acids such as, for example, caproic acid, caprylic acid, capric acid, lauric acid, myristic acid, palmatic acid, palmitoleic acid, isostearic acid, stearic acid, 12-hydroxystearic acid, dihydroxystearic acid, oleic acid, linoloic acid, petroselic acid, elaidic acid, arachic acid, behenic acid, erucic acid, gadoleic acid, linolenic acid, eicosapentaoic acid, docosahexaoic acid or arachidonic acid, alone or in a mixture. The radical $R^7$ can also be the acyl radical of polycondensation products of hydroxy-functionalized acids, for example poly-12-hydroxystearic acid or polyricinolic acid. The acyl radical used as radical $R^7$ may be technical-grade mixtures, for example mixtures of natural fatty acids, e.g., rapeseed oil fatty acid, soya oil fatty acid, sunflower oil fatty acid, tallow oil fatty acid, palm oil fatty acid, palm kernel oil fatty acid, coconut fatty acid, which may be subject to deviations in their precise composition depending on their specific source and the purification methods used, and can also comprise typical secondary constituents, such as unsaturated, functionalized or branched components. Moreover, it is also possible to use mixtures of acids of another origin, for example based on petrochemical processes.

Further preferred embodiments are compounds in which:
N is 80 to 120, preferably 90 to 110, in particular 100 and
a is 60 to 100, preferably 65 to 85, in particular 73 and
b is 10 to 30, preferably 12 to 20, in particular 16 and
c is 5 to 20, preferably 8 to 15, in particular 9 and
d=e=f is 0 and
$R^1$=$R^2$ is CH$_3$ and
m is 1 and
n is 1 and
p is 0 and
$R^7$ is the acyl radical of a fatty acid having 8 to 18 carbon atoms, preferably having 12 to 14 carbon atoms, or a mixture thereof, in particular the acyl radical of a hydrogenated coconut fatty acid, i.e. a technical-grade mixture of predominantly lauric acid and myristic acid
q is 1 and
Y is OH and
Z is H, or N is 80 to 120, preferably 90 to 110, in particular 100 and
a is 60 to 100, preferably 65 to 85, in particular 73 and
b is 10 to 30, preferably 12 to 20, in particular 16 and
c is 5 to 20, preferably 8 to 15, in particular 9 and
d=e=f is 0 and
$R^1$=$R^2$ is CH$_3$ and
m is 1 and
n is 1 and
p is 1 and
$R^7$ is the acyl radical of a fatty acid having 8 to 18 carbon atoms, preferably having 12 to 14 carbon atoms, or a mixture thereof, in particular the acyl radical of a hydrogenated coconut fatty acid and
$R^8$ is H and
q is 1 and
Y is OH and
Z is H, or N is 80 to 120, preferably 90 to 110, in particular 100 and
a is 60 to 100, preferably 65 to 85, in particular 73 and
b is 10 to 30, preferably 12 to 20, in particular 16 and
c is 5 to 20, preferably 8 to 15, in particular 9 and
d=e=f is 0 and
$R^1$=$R^2$ is CH$_3$ and
m is 4 and
n is 0 and
p is 0 and
$R^7$ is the acyl radical of a fatty acid having 8 to 18 carbon atoms, preferably having 12 to 14 carbon atoms, or a mixture thereof, in particular the acyl radical of a hydrogenated coconut fatty acid, and
q is 1 and
Y is OH and
Z is H.

The inventive siloxanes modified with organic esters can be prepared by hydrosilylation. The terminally unsaturated esters used for the hydrosilylation can be obtained by esterification or transesterification of the corresponding alcohols with acids, as explained, for example, in German Patent Application No. DE 10 2006 005100.9. The SiH-functional siloxanes used for the hydrosilylation are obtainable by the methods of equilibration known to the person skilled in the art. See, for example, U.S. Pat. No. 7,196,153 B2.

Hydrosilylation can be carried out in accordance with established methods in the presence of a catalyst. In this regard, it is possible, for example, to use catalysts, such as platinum complexes, rhodium complexes, osmium complexes, ruthenium complexes, palladium complexes, iridium complexes or similar compounds or the corresponding pure elements or their derivatives immobilized on silica, aluminium oxide or activated carbon or similar support materials. The hydrosilylation can be carried out in the presence of Pt catalysts, such as cis-platinium or Karstedt catalyst [tris(divinyltetramethyldisiloxane)bis-platinum]. The amount of catalyst used can be $10^{-7}$ to $10^{-1}$ mol per mole of olefin, preferably 1 to 20 ppm. The hydrosilylation can be carried out at temperatures between 0° and 200° C., preferably between 50° and 140° C. The reaction can be carried out in suitable solvents, such as aliphatic or aromatic hydrocarbons, cyclic oligosiloxanes, alcohols or esters. It is also possible to dispense with the use of a solvent.

The emulsifier systems according to the invention are preferably used as water-in-oil, oil-in-water or water-in-silicone emulsifiers or dispersion auxiliaries. Water-in-oil, oil-in-water and water-in-silicone emulsions and dispersions obtained with the help of the emulsifier systems according to the invention are also provided by the invention.

The invention further provides the use of the emulsifier systems according to the invention for producing cosmetic, dermatological or pharmaceutical formulations. The cosmetic, dermatological or pharmaceutical formulations are thus also provided by the invention.

The invention further provides the use of the emulsifier systems for producing care and cleaning compositions, containing optionally dispersed solids, for domestic use or industry, in particular for hard surfaces, leather or textiles. The care and cleaning compositions for domestic use or industry and the care and cleaning compositions for hard surfaces, leather or textiles are thus also provided by the invention.

The cosmetic, dermatological or pharmaceutical formulations and also the care and cleaning compositions can comprise, for example, at least one additional component selected from the group of:
 Emollients,
 Coemulsifiers and surfactants,
 Thickeners/viscosity regulators/stabilizers,
 UV photoprotective filters,
 Antioxidants,
 Hydrotropes (or polyols),
 Solids,
 Pearlescence additives,
 Deodorants and antiperspirant active ingredients,
 Insect repellents,
 Self-tanning agents,
 Preservatives,
 Conditioners,
 Perfumes,
 Dyes,
 Biogenic active ingredients,
 Care additives, and/or
 Solvents.

Emollients that can be used in the present invention are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. It is also possible to use the esterification products of aliphatic, difunctional alcohols having 2 to 36 carbon atoms with monofunctional aliphatic carboxylic acids having 1 to 22 carbon atoms. Furthermore, long-chain arylic acid esters, such as, for example, esters of benzoic acid, e.g., benzoic acid esters of linear or branched, saturated or unsaturated alcohols having 1 to 22 carbon atoms, and also isostearyl benzoate or octyldodecyl benzoate, are suitable. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters which are obtainable from technical-grade aliphatic alcohol cuts and technical-grade, aliphatic carboxylic acid mixtures, e.g., esters of unsaturated fatty alcohols having 12 to 22 carbon atoms and saturated and unsaturated fatty acids having 12 to 22 carbon atoms, as are accessible from animal and vegetable fats. However, naturally occurring monoester or wax ester mixtures, as are present, for example, in jojoba oil or in sperm oil, are also suitable for use in the present invention. Suitable dicarboxylic acid esters are, for example, di-n-butyl adipate, di-n-butyl sebacate, di(2-ethylhexyl) adipate, di(2-hexyldecyl)succinate, D-isotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl glycol dicaprylate. Further fatty acid esters that can be used as emollients in the invention are, for example, $C_{12-15}$ alkyl benzoate, dicaprylyl carbonate, diethylhexyl carbonate.

As emollients and an oil component it is also possible to use relatively long chain triglycerides, i.e., triple esters of glycerol with three acid molecules, of which at least one is relatively long-chain. Here, mention may be made by way of example of fatty acid triglyceride; as such, it is possible to use, for example, natural, vegetable oils, e.g., olive oil, sunflower oil, soya oil, peanut oil, rapeseed oil, almond oil, sesame oil, avocado oil, castor oil, cocoa butter, palm oil, but also the liquid fractions of coconut oil or of palm kernel oil, and also animal oils, such as, for example, neatsfoot oil, the liquid fractions of beef tallow or also synthetic triglycerides of caprylic/capric acid mixtures, triglycerides of technical-grade oleic acid, triglycerides with isostearic acid, or of palmitic acid/oleic acid mixtures as emollients and oil components. In addition, hydrocarbons, in particular also liquid paraffins and isoparaffins, can be used. Examples of hydrocarbons that can be used are paraffin oil, isohexadecane, polydecene, vaseline, paraffin perliquidum, squalane, and ceresin. Furthermore, it is also possible to use linear or branched fatty alcohols, such as oleyl alcohol or octyldodecanol, and also fatty alcohol ethers, such as dicaprylyl ether. Suitable silicone oils and silicone waxes are, for example, polydimethylsiloxanes, cyclomethylsiloxanes, and also aryl- or alkyl- or alkoxy-substituted polymethyl siloxanes or cyclomethylsiloxanes.

Coemulsifiers or surfactants that can be used in the invention are non-ionic, anionic, cationic or amphoteric surfactants.

Nonionogenic coemulsifiers or surfactants that can be used in the invention are compounds from at least one of the following groups:

addition products of from 2 to 100 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12/18}$ fatty acid mono- and diesters of addition products of from 1 to 100 mol of ethylene oxide onto glycerol, glycerol mono- and diesters and sorbitan mono- and diesters of saturated and unsaturated fatty acids having 6 to 22 carbon atoms and ethylene oxide addition products thereof alkyl mono- and oligoglycosides having 8 to 22 carbon atoms in the alkyl radical and ethylene oxide addition products thereof, addition products of from 2 to 200 mol of ethylene oxide onto castor oil and/or hydrogenated castor oil, partial esters based on linear, branched, unsaturated or saturated $C_6$-$C_{22}$-fatty acids, ricinoloic acid, and 12-hydroxystearic acid and glycerol, polyglycerol, pentaerythritol, dipentaerythritol, sugar alcohols (e.g., sorbitan), alkyl glucosides (e.g., methyl glucoside, butyl glucoside, lauryl glucoside), and polyglucosides (e.g., cellulose), mono-, di- and trialkyl phosphates, and mono-, di- and/or tri-PEG-alkyl phosphates and salts thereof polysiloxane-polyether copolymers (dimethicone copolyols), such as, for example, PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15, polysiloxane-polyalkyl-polyether copolymers or corresponding derivatives, such as, for example, lauryl or cetyl dimethicone copolyols, in particular cetyl PEG/PPG-10/1 dimethicone (ABIL® EM 90 (Degussa)), mixed esters of pentaerythritol, fatty acids, citric acid and fatty alcohol as in DE 11 65 574 and/or mixed esters of fatty acids having 6 to 22 carbon atoms, methylglucose and polyols, preferably glycerol or polyglycerol, citric acid esters, such as, for example, glycerol stearate citrate, glycerol oleate citrate and dilauryl citrate.

Anionic coemulsifiers or surfactants can comprise water-solubilizing anionic groups, such as, for example, a carboxylate, sulfate, sulfonate or phosphate group and a lipophilic radical. Skin compatible anionic surfactants are known in large numbers to the person skilled in the art and are commercially available; they may be alkyl sulfates or alkyl phosphates in the form of their alkali metal, ammonium or alkanolammonium salts, alkyl ether sulfates, alkyl ether carboxylates, acyl sarcosinate, and sulfosuccinates and acyl glutamates in the form of their alkali metal or ammonium salts.

Cationic coemulsifiers and surfactants can also be added. As such, quaternary ammonium compounds, in particular those provided with at least one linear and/or branched, saturated or unsaturated alkyl chain having 8 to 22 carbon atoms, in particular, can be used, thus, for example, alkyl trimethylammonium halides, such as, for example, cetyltrimethylammonium chloride or bromide or behenyltrimethylammonium chloride, but also dialkyldimethylammonium halides, such as, for example, distearyldimethylammonium chloride.

Furthermore, monoalkylamidoquats, such as, for example, palmitamidopropyltrimethylammonium chloride or corresponding dialkylamidoquats, can be used.

Furthermore, it is also possible to use readily biodegradable quaternary ester compounds, which may be quaternized fatty acid esters based on mono-, di- or triethanolamine. Furthermore, alkylguanidinium salts can be added as cationic emulsifiers.

In addition, it is possible to use amphoteric surfactants, such as, for example, betaines, amphoacetates or amphopropionates, together with the polyglycerol esters according to the invention.

Suitable thickeners for thickening oil phases are all of the thickeners known to the person skilled in the art. Particularly mentioned are waxes, such as hydrogenated castor wax, bees wax or microwax. Furthermore, it is also possible to use inorganic thickeners, such as silica, alumina or sheet silicates (e.g., hectorite, laponite, and saponite). These inorganic oil phase thickeners can be hydrophobically modified. For the thickening/stabilization of water-in-oil emulsions, it is possible to use, in particular, aerosols, sheet silicates and/or metal salts of fatty acids, such as, for example, zinc stearate.

As viscosity regulators for aqueous surfactant systems, e.g., NaCl, low molecular weight non-ionic surfactants, such as cocoamides DEA/MEA and Laureth-3, or polymeric, high molecular weight, associative, highly ethoxylated fatty derivatives, such as PEG-200 hydrogenated glycerol palmate may be present.

UV photoprotective filters that may be used in the invention are, for example, organic substances which are able to absorb ultraviolet rays and give off the absorbed energy again in the form of longer-wave radiation, e.g., heat. UVB filters may be oil-soluble or water-soluble. Examples of oil-soluble UVB photoprotective filters are:

3-benzylidenecamphor and derivatives thereof, e.g., 3-(4-methyl-benzylidene)camphor, 4-aminobenzoic acid derivatives, such as, for example, 2-ethylhexyl 4-(dimethylamino)benzoate, 2-ethylhexyl 4-(dimethylamino)benzoate and amyl 4-(dimethyl-amino)benzoate, esters of cinnamic acid, such as, for example, 2-ethylhexyl 4-methoxycinnamate, isopentyl 4-methoxycinnamate, 2-ethylhexyl 2-cyano-3-phenylcinnam(octocrylene), esters of salicylic acid, such as, for example, 2-ethylhexyl salicylate, 4-isopropylbenzyl salicylate, homomethyl salicylate, derivatives of benzophenone, such as, for example, 2-hydroxy-4-methoxybenzophenone, 2-hydroxy-4-methoxy-4'-methylbenzophenone, 2,2'-dihydroxy-4-methoxybenzophenone, esters of benzylmalonic acid, such as, for example, di-2-ethylhexyl 4-methoxybenzmalonate, triazine derivates, such as, for example, 2,4,6-trianilino(p-carbo-2'-ethyl-1'-hexyloxy)-1,3,5-triazine and octyltriazone, propane-1,3-diones, such as, for example, 1-(4-tert-butylphenyl)-3-(4'-methoxyphenyl)propane-1,3-dione.

Suitable water-soluble UVB photoprotective filters are:

2-phenylbenzimidazole-5-sulfonic acid and the alkali metal, alkaline earth metal, ammonium, alkylammonium, alkanolammonium and glucammonium salts thereof, sulfonic acid derivatives of benzophenone, such as, for example, 2-hydroxy-4-methoxybenzophenone-5-sulphonic acid and its salts, sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UVA photoprotective filters are, in particular, derivatives of benzoylmethane, such as, for example, 1-(4'-tert-butylphenyl)-3-(4'-methoxy-phenyl)propane-1,3-dione or 1-phenyl-3-(4'-isopropylphenyl)propane-1,3-dione. The UV-A and UV-B filters can of course also be used in mixtures.

Besides the specified soluble substances, insoluble pigments are also suitable for this purpose, namely finely dispersed metal oxides or salts, such as, for example, titanium dioxide, zinc oxide, iron oxide, aluminium oxide, cerium oxide, zirconium oxide, silicates (talc), barium sulphate and zinc stearate. The particles here should have an average diameter of less than 100 nm, e.g., between 5 and 50 nm and in particular between 15 and 30 nm. They can have a spherical shape, although it is also possible to use particles that have an ellipsoidal shape or a shape which deviates in some other way from the spherical configuration. A relatively new class of photoprotective filters are micronized organic pigments, such as, for example, 2,2'-methylenebis-{6-(2H-benzotriazol-2-yl)-4-(1,1,3,3-tetramethylbutyl)phenol} with a particle size of less than 200 nm, which is obtainable, for example, as 50% strength aqueous dispersion.

Further suitable WV photoprotective filters can be found in the overview by P. Finkel in SÖFW-Journal 122, 543 (1996).

Besides the two aforementioned groups of primary UV photoprotective filters, it is also possible to use secondary photoprotective filters of the antioxidant type; these interrupt the photochemical reaction chain which is triggered when UV radiation penetrates into the skin. Antioxidants which may be used are, for example, superoxide dismutase, tocopherols (vitamin E), dibutylhydroxytoluene and ascorbic acid (vitamin C).

Hydrotropes that can be used to improve the flow behavior and the application properties are, for example, ethanol, isopropyl alcohol or polyols. Polyols which are contemplated in the invention can have 2 to 15 carbon atoms and at least two hydroxyl groups. Typical examples are:

glycerol, alkylene glycols, such as, for example, ethylene glycol, diethylene glycol, propylene glycol, butylene glycol, hexylene glycol, and polyethylene glycols with an average molecular weight of from 100 to 1000 Daltons, technical-grade oligoglycerol mixtures with a degree of self-condensation of from 1.5 to 10, such as, for example, technical-grade diglycerol mixtures with a diglycerol content of from 40 to 50% by weight, methylol compounds, such as, in particular, trimethylolethane, trimethylolpropane, trimethylolbutane, pentaerythritol and dipentaerythritol, lower alkyl glucosides, in particular those with 1 to 4 carbon atoms in the alkyl radical, such as, for example, methyl glucoside and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Solids that may be used in the invention are, for example, iron oxide pigments, titanium dioxide or zinc oxide particles and those specified additionally under "UV protectants". Furthermore, it is also possible to use particles which lead to special sensory effects, such as, for example, nylon-12, boron nitride, polymer particles, such as, for example, polyacrylate or polymethyl acrylate particles or silicone elastomers.

Pearlescence additives that can be used are, for example, glycerol distearates or PEG-3 distearate.

Suitable deodorant active ingredients are, for example, odor concealers, such as the customary perfume constituents, odor absorbers, for example the sheet silicates described in the Patent Laid-Open Specification DE 40 09 347, of these, in particular, montmorillonite, kaolinite, illite, beidelite, nontronite, saponite, hectorite, bentonite, smectite, also, for example, zinc salts of ricinolic acid. Antibacterial agents are likewise suitable to be incorporated. Antibacterial substances are, for example, 2,4,4'-trichloro-2'-hydroxydiphenyl ether (Irgasan), 1,6-di-(4-chlorophenylbiguanido)hexane (chlorhexidin), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), ethylhexyl glycerol ether, polyglyceryl-3 caprylate (TEGO® Cosmo P813, Degussa), and also the active agents described in the Patent Laid-Open Specifications DE 198 55 934, DE 37 40 186, DE 39 38 140, DE 42 04 321, DE 42 29 707, DE 42 29 737, DE 42 38 081, DE 43 09 372, DE 43 24 219 and EP 666 732.

Antiperspirant active ingredients that may be used are astringents, for example basic aluminium chlorides, such as aluminium chlorohydrate ("ACH") and aluminium zirconium glycine salts ("ZAG").

Insect repellents that can be used in the invention are, for example, N,N-diethyl-m-toluamide, 1,2-pentanediol or Insect Repellent 3535.

Self-tanning agents that can be used are, for example, dihydroxyacetone and erythrulose.

Preservatives that can be used are, for example, mixtures of individual or a plurality of alkylparaben esters with phenoxyethanol. The alkylparaben esters may be methylparaben, ethylparaben, propylparaben and/or butylparaben. Instead of phenoxyethanol, it is also possible to use other alcohols, such as, for example, benzyl alcohol or ethanol. Moreover, it is also possible to use other customary preservatives, such as, for example, sorbic acid or benzoic acid, salicylic acid, 2-bromo-2-nitropropane-1,3-diol, chloroacetamide, diazolidinylurea, DMDM hydantoin, iodopropynyl butylcarbamate, sodium hydroxymethylglycinate, methylisothiazoline, chloromethylisothiazoline, ethylhexylglycerol or caprylyl glycol.

Conditioners that can be used are, for example, organic quaternary compounds, such as cetrimonium chloride, dicetyldimonium chloride, behentrimonium chloride, distearyldimonium chloride, behentrimonium methosulphate, distearoylethyldimonium chloride, palmitamidopropyltrimonium chloride, guar hydroxypropyltrimonium chloride, hydroxypropylguar hydroxypropyltrimonium chloride, or quaternium-80 or also amine derivatives, such as, for example, aminopropyldimethicones or stearamidopropyldimethylamines.

Perfume oils that can be used are natural or synthetic fragrances or mixtures thereof. Natural fragrances are extracts from flowers (lily, lavender, rose, jasmine, neroli, ylang-ylang), stems and leaves (geranium, patchouli, petitgrain), fruits (anise, coriander, caraway, juniper), fruit peels (bergamot, lemons, oranges), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Furthermore, animal raw materials are suitable, such as, for example, civet and castoreum. Typical synthetic fragrance compounds are products of the ester, ether, aldehyde, ketone, alcohol and hydrocarbon types. Fragrance compounds of the ester type are, for example, benzyl acetate, phenoxyethyl isobutyrate, p-tert-butyl cyclohexylacetate, linalyl acetate, dimethylbenzylcarbinyl acetate, phenylethyl acetate, linalyl benzoate, benzyl formiate, ethylmethyl phenylglycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethole, citronellol, eugenol, isoeugenol, geraniol, linalool, phenylethyl alcohol and terpineol, the hydrocarbons include primarily the terpenes and balsams. It is possible to use mixtures of different fragrances that together produce a pleasing scent note.

Essential oils of low volatility, which are mostly used as aroma components, are also suitable as perfumes, e.g., sage oil, camomile oil, oil of cloves, melissa oil, mint oil, cinnamon leaf oil, linden blossom oil, juniper berry oil, vetiver oil, oliban oil, galbanum oil, labolanum oil and lavandin oil. It is possible to use bergamot oil, dihydromyrcenol, lilial, lyral, citronellol, phenylethyl alcohol, α-hexylcinnamaldehyde, geraniol, benzyl acetate, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix cocur, iso-E-super, fixolide NP, evernyl, iraldein gamma, phenylacetic acid, geranyl acetate, benzyl acetate, rose oxide, romillat, irotyl and floramat alone or in mixtures.

Dyes that can be used are the substances that are approved and suitable for cosmetic purposes, as are listed, for example, in the publication "Kosmetische Färbemittel"[Cosmetic Colorants] from the Dyes Commission of the German Research Society, Verlag Chemie, Weinheim, 1984, pp. 81 to 106. These dyes are usually used in concentrations of from 0.001 to 0.1% by weight, based on the total mixture.

Biogenic active ingredients are to be understood as meaning, for example, tocopherol, tocopherol acetate, tocopherol palmitate, ascorbic acid, desoxyribonucleic acid, Coenzym Q10, retinol, bisabolol, allantoin, phytantriol, panthenol, AHA acids, amino acids, hyaluronic acid, creatine (and creatine derivates), guanidine (and guanidine derivates), ceramides, phytosphingosine (and phytosphingosine derivates), sphingosine (and sphingosine derivates), pseudoceramides, essential oils, peptides, protein hydrolysates, plant extracts, and vitamin complexes.

Care additives that may be present are, for example, ethoxylated glycerol fatty acid esters, such as, for example, PEG-7 glycerol cocoate, or cationic polymers, such as, for example, polyquaternium-7 or polyglycerol esters.

Solvents that can be used are, for example, propylene glycol, dipropylene glycol, glycerol, glycerol carbonate, water, ethanol, propanol, 1,3-propanediol.

Preference is given to the use of emulsifier systems according to the invention for producing cosmetic or pharmaceutical formulations. Formulations, which are given a readily spreadable consistency through use of oil-in-water or water-in-oil emulsifiers because, as a result of these emulsifier systems, an oil or a fat can be readily incorporated into an aqueous phase or an aqueous phase can be readily incorporated into an oil or a fat, may be, for example, creams, such as care creams, baby creams or sun protection creams, ointments, lotions or make-up. In particular, the cosmetic formulations may also be formulations which comprise dispersed solids, such as, for example, iron oxide pigments, titanium dioxide or zinc oxide particles. In pharmaceutical preparations, such as ointments or creams, oil-in-water or water-in-oil emulsifiers are required for the application of active ingredients.

Formulations according to the invention can therefore be used as skincare product, face care product, head care product body care product, intimate care product, foot care product, hair care product, nail care product, dental care product or oral care product.

Formulations according to the invention can be used in the form of an emulsion, a suspension, a solution, a cream, an ointment, a paste, a gel, an oil, a powder, an aerosol, a stick, a spray, a cleaning product, a make-up or sunscreen preparation or a face toner.

The examples listed below describe the present invention by way of example without any intention to restrict the invention, the breadth of application of which arises from the description in its entirety and the claims, to the embodiments specified in the examples.

EXAMPLES

Example 1

Enzymatic Synthesis of Allyloxyethanol Coconut Fatty Acid Ester According to DE 10 2006 005100.9

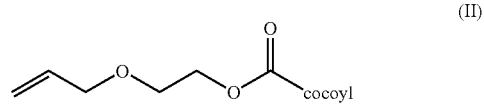

(II)

134.8 g of allyloxyethanol and 243.9 g of coconut fatty acid (Edenor HK 8-18, Cognis, Monheim, Germany) were initially introduced into a multi-neck round-bottomed flask and heated to 40° C. After adding 18 g of Novozym 435 (immobilized lipase B from *C. antarctica*, obtained from Novozymes A/S, Bagsvaerd, Denmark), a vacuum was applied (20 mbar) and the water of reaction was distilled off. After 10 hours, the immobilized enzyme was filtered off. The filtrate produced at 344 g of product without further work-up as a colorless liquid.

Example 2

Enzymatic Synthesis of 1-Allylglyceryl Coconut Fatty Acid Ester According to DE 10 2006 005100.9

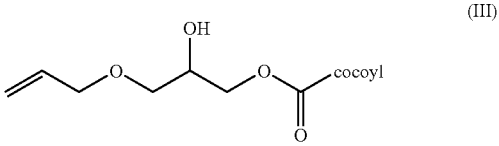

(III)

185.1 g of 1-allylglycerol and 213.4 g of coconut fatty acid (Edenor HK 8-18, Cognis, Monheim, Germany) were initially introduced into a multi-neck round-bottomed flask and heated to 50° C. After adding 19 g of Novozym 435, a vacuum was applied (20 mbar) and the water of reaction was distilled off. After 7 hours, the immobilized enzyme was filtered off. The filtrate produced 379 g of product without further work-up as a colorless liquid.

Example 3

Enzymatic Synthesis of Coconut Fatty Acid Hexenyl Ester According to DE 10 2006 005100.9

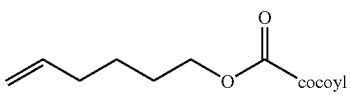
(IV)

140.0 g of hex-5-en-1-ol and 258.1 g of coconut fatty acid (Edenor HK 8-18, Cognis, Monheim, Germany) were initially introduced into a multi-neck round-bottomed flask and heated to 60° C. After adding 19 g of Novozym 435, a vacuum was applied (20 mbar) and the water of reaction was distilled off. After 7 hours, the immobilized enzyme was filtered off. The filtrate produced 360 g of product without further work-up as a colorless liquid.

Example 4

Hydrosilylation of the Reaction Product of Example 1

Preparation of a polysiloxane according to the invention of the general formula (V):

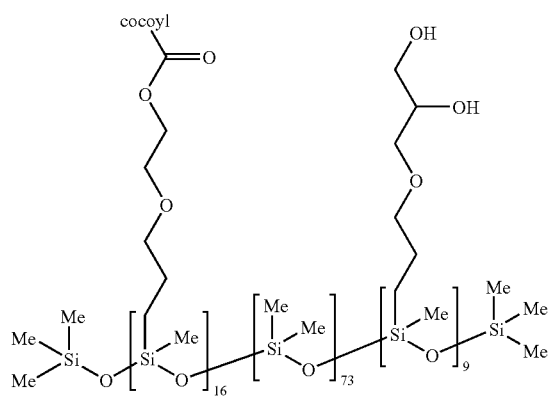
(V)

6.2 g (47 mmol) of glycerol monoallyl ether, 23.8 g (83 mmol) of the allyloxyethanol coconut fatty acid ester from Example 1 and 10 ppm of Karstedt catalyst were initially introduced into a four-neck flask equipped with stirrer, dropping funnel, thermometer and reflux condenser and heated to 95° C. 28.9 g (100 mmol of SiH) of an SiH-siloxane of the general formula (VI)

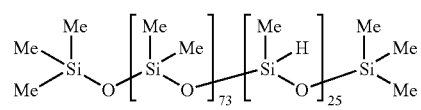
(VI)

where added dropwise and the batch was stirred for 1 h at 95° C. According to SiH value determination, complete conversion of the SiH-siloxane was obtained. Volatile fractions were then distilled off in vacuo at 110° C. A viscous, slightly cloudy, virtually colorless product was obtained.

Example 5

Hydrosilylation of the Reaction Product of Example 2

Preparation of a polysiloxane according to the invention of the general formula (VII):

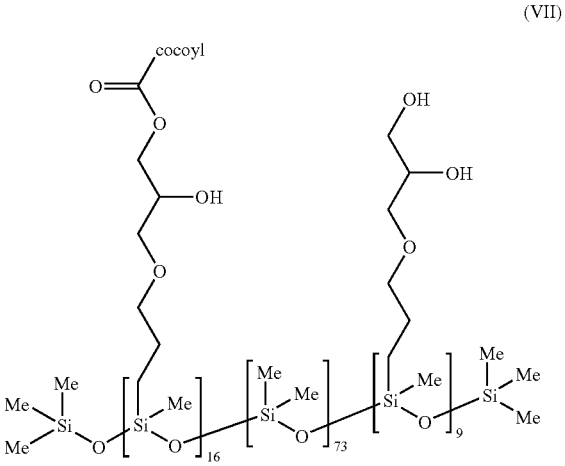
(VII)

6.2 g (47 mmol) of glycerol monoallyl ether, 22.5 g (83 mmol) of the 1-allylglyceryl coconut fatty acid ester from Example 2 and 10 ppm of Karstedt catalyst were initially introduced into a four-neck flask equipped with stirrer, dropping funnel, thermometer and reflux condenser, and heated to 95° C. 28.9 g (100 mmol of SiH) of a SiH-siloxane of the general formula (VI) were added dropwise and the batch was stirred for 1 h at 95° C. According to SiH value determination, complete conversion of the SiH-siloxane was obtained. Volatile fractions were then distilled off in vacuo at 110° C. A viscous, slightly cloudy, virtually colourless product was obtained.

Example 6

Hydrosilylation of the reaction product from Example 3

Preparation of a polysiloxane according to the invention of the general formula (VIII):

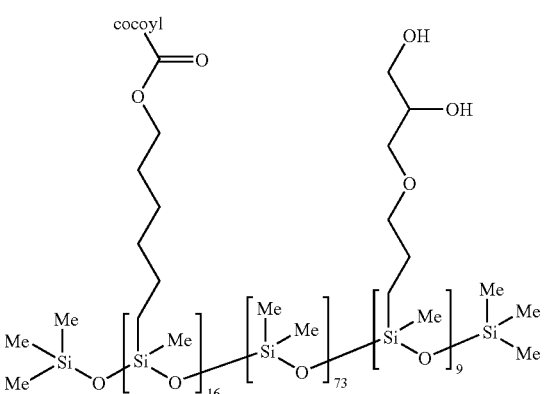
(VIII)

6.2 g (47 mmol) of glycerol monoallyl ether, 23.6 g (83 mmol) of the coconut fatty acid hexenyl ester from Example 3 and 10 ppm of Karstedt catalyst were initially introduced into a four-neck flask equipped with stirrer, dropping funnel, thermometer and reflux condenser, and heated to 95° C. 28.9 g (100 mmol of SiH) of an SiH-siloxane of the general formula (VI) were added dropwise and the batch was stirred for 1 h at 95° C. According to SiH value determination, complete conversion of the SiH-siloxane was obtained. Volatile fractions were then distilled off in vacuo at 110° C. A viscous, slightly cloudy, virtually colourless product was obtained.

Application Examples

The described cosmetic emulsions are intended to serve to illustrate the usability of the ester-modified organopolysiloxanes as emulsifiers for cosmetic emulsions by way of example.

Formulations 1 to 6 are W/O emulsions prepared by a hot method, and formulations 7 to 9 are W/O emulsions prepared by a cold method. The preparation was carried out in each case by introducing the water phase into the oil phase and subsequent homogenization in accordance with customary methods.

Nomenclature in accordance with INCI:

|  | 1 | 2 | 3 |
|---|---|---|---|
| Polysiloxane Ex. 4 | 2.0% | | |
| Polysiloxane Ex. 5 | | 2.0% | |
| Polysiloxane Ex. 6 | | | 2.0% |
| Hydrogenated castor oil | 0.1% | 0.1% | 0.1% |
| Microcrystalline wax | 0.1% | 0.1% | 0.1% |
| Paraffinum perliquidum | 118% | 11.8% | 11.8% |
| Ethylhexyl palmitate | 6.0% | 6.0% | 6.0% |
| NaCl | 0.8% | 0.8% | 0.8% |
| Glycerin | 3.1% | 3.1% | 3.1% |
| Water | 76.0% | 76.0% | 76.0% |
| 2-Bromo-2-nitropropane-1,3-diol | 0.1% | 0.1% | 0.1% |

|  | 4 | 5 | 6 |
|---|---|---|---|
| Polysiloxane Ex. 4 | 2.0% | | |
| Polysiloxane Ex. 5 | | 2.0% | |
| Polysiloxane Ex. 6 | | | 2.0% |
| Hydrogenated castor oil | 0.1% | 0.1% | 0.1% |
| Microcrystalline wax | 0.1% | 0.1% | 0.1% |
| Caprylic/capric triglyceride | 8.9% | 8.9% | 8.9% |
| Ethylhexyl palmitate | 8.9% | 8.9% | 8.9% |
| NaCl | 0.8% | 0.8% | 0.8% |
| Glycerin | 3.1% | 3.1% | 3.1% |
| Water | 76.0% | 76.0% | 76.0% |
| 2-Bromo-2-nitropropane-1,3-diol | 0.1% | 0.1% | 0.1% |

|  | 7 | 8 | 9 |
|---|---|---|---|
| Polysiloxane Ex. 4 | 2.5% | | |
| Polysiloxane Ex. 5 | | 2.5% | |
| Polysiloxane Ex. 6 | | | 2.5% |
| Zinc stearate | 0.5% | 0.5% | 0.5% |
| Decyl oleate | 8.0% | 8.0% | 8.0% |
| Caprylic/capric triglyceride | 8.0% | 8.0% | 8.0% |
| Diethylhexyl carbonate | 6.0% | 6.0% | 6.0% |
| NaCl | 0.5% | 0.5% | 0.5% |
| Water | 74.4% | 74.4% | 74.4% |
| 2-Bromo-2-nitropropane-1,3-diol | 0.1% | 0.1% | 0.1% |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An emulsifier system comprising a modified siloxane of general formula (I)

$$
\begin{array}{c}
R^1 \\
R^1-\underset{|}{\overset{R^2}{\text{Si}}}-O-\left[\underset{|}{\overset{R^1}{\text{Si}}}-O\right]_a-\left[\underset{|}{\overset{R^1}{\text{Si}}}-O\right]_b-\left[\underset{|}{\overset{R^1}{\text{Si}}}-O\right]_c-\left[\underset{|}{\overset{R^1}{\text{Si}}}-O\right]_d- \\
R^1 \\
\left[\underset{|}{\overset{R^1}{\text{Si}}}-O\right]_e-\left[\underset{|}{\overset{R^6}{\text{Si}}}-O\right]_f-\underset{|}{\overset{R^2}{\text{Si}}}-R^1 \\
R^1
\end{array}
\tag{I}
$$

where
  N is $a+b+c+d+e+f+2=20$ to 250,
  a is 1 to 230,
  b is 1 to 100,
  c is 1 to 100,
  d is 0 to 50,
  e is 0 to 10,
  f is 0 to 10,
  $R^1$ independently of the others is identical or different and is selected from the group consisting of saturated or unsaturated alkyl groups having 1 to 30 carbon atoms, alkaryl radicals having 7 to 30 carbon atoms, and aryl radicals having 6 to 30 carbon atoms,
  $R^2$ independently of the others is identical or different and is selected from the group $R^1$, $R^3$, $R^4$ or $R^5$,
  $R^3$ independently of the others is identical or different ester radicals of general formula (Ia)

$$
\begin{array}{c}
\xi\!\!\!\!\sim\!\!\!\text{---}\!\!\left[\text{---}\right]_m\!\!\text{---O}\!\!\left[\text{---}\underset{|}{\overset{\text{OR}^8}{\phantom{C}}}\text{---}\right]_p\!\!\!\text{---OR}^7 \\
\end{array}_n
\tag{Ia}
$$

where
  m is 1 to 4,
  n is 0 or 1,
  p is 0 or 1,
  $R^7$ is the acyl radicals of monobasic, saturated or unsaturated, linear or branched fatty acids having 6 to 30 carbon atoms,
  $R^8$ is hydrogen or $R^7$,
  $R^4$ is the radicals of the general formula (Ib)

$$
\xi\!\!\!\!\sim\!\!\!\text{---}\text{---}\text{---O}\!\!\left[\text{---}\underset{|}{\overset{Y}{\phantom{C}}}\underset{|}{\overset{Z}{\phantom{C}}}\text{---}\right]_q\!\!\!\text{---OH}
\tag{Ib}
$$

where
  q is 1 to 20,
  Y and Z, independently of one another, are identical or different radicals selected from the group —H, —OH, —CH$_3$, —CH$_2$CH$_3$ or —CH$_2$OH, where at least one radical must be from the group —OH or —CH$_2$OH, $R^5$ independently of the others is saturated or unsaturated alkyl groups having 1 to 30 carbon atoms or alkaryl radicals having 7 to 30 carbon atoms, $R^6$ independently of the others is identical or different radicals of the general formula (Ic)

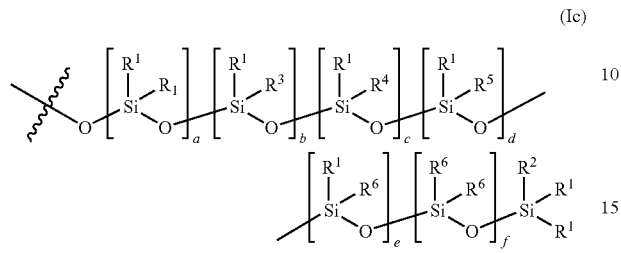

where a, b, c, d, e, f, $R^1$, $R^2$, $R^3$, $R^4$, $R^5$ and $R^6$ are as defined above.

2. The emulsifier system according to claim 1 where

N a+b+c+d+e+f+2=50 to 150,
a is 10 to 130,
b is 5 to 30,
c is 5 to 30,
d is 0,
e is 0,
f is 0,
$R^1$ is alkyl groups having 1 to 4 carbon atoms,
$R^2$ is $R^1$,
m is 1 or 4,
n is 0 or 1,
p is 0 or 1,
$R^7$ is the acyl radicals of monobasic, saturated or unsaturated, linear or branched fatty acids having 8 to 22 carbon atoms,
$R^8$ is hydrogen,
q is 1,
Y is —OH and
Z is —H.

3. A water-in-oil emulsion comprising at least one emulsifier system according to claim 1.

4. An oil-in-water emulsion comprising at least one emulsifier system according to claim 1.

5. A water-in-silicon emulsion comprising at least one emulsifier system according to claim 1.

6. A dispersion comprising at least the emulsifier system of claim 1.

7. A formulation comprising at least the emulsifier system of claim 1.

8. The formulation of claim 7 which is a cosmetic formulation.

9. The formulation of claim 7 which is a dermatological formulation.

10. The formulation of claim 7 which is a pharmaceutical formulation.

11. A composition comprising at least said emulsifier system of claim 1.

12. The composition of claim 11 which is a care composition.

13. The composition of claim 11 which is a cleaning composition.

14. The emulsifier system of claim 1 wherein said modified siloxane is polyether-free.

15. The emulsifier system of claim 1 wherein
N is 80 to 120,
a is 60 to 100,
b is 10 to 30,
c is 5 to 20,
d=e=f is 0,
$R^1$=$R^2$ is $CH_3$,
m is 1,
n is 1,
p is 0,
$R^7$ is the acyl radical of a fatty acid having 8 to 18 carbon atoms,
q is 1,
Y is OH, and
Z is H.

16. The emulsifier system of claim 1 wherein
N is 80 to 20,
a is 6 to 100,
b is 1 to 30,
c is 5 to 20,
d=e=f is 0,
$R^1$=$R^2$ is $CH_3$,
m is 1,
n is 1,
p is 1,
$R^7$ is the acyl radical of a fatty acid having 8 to 18 carbon atoms,
$R^8$ is H,
q is 1,
Y is OH,
Z is H.

17. The emulsifier system of claim 1 wherein
N is 80 to 120,
a is 60 to 100,
b is 10 to 30,
c is 5 to 20,
d=e=f is 0,
$R^1$=$R^2$ is $CH_3$,
m is 4,
n is 0,
p is 0,
$R^7$ is the acyl radical of a fatty acid having 8 to 18 carbon atoms,
q is 1,
Y is OH, and
Z is H.

* * * * *